Dec. 16, 1969 C. G. KLEHM Plant Pat. 2,955
PEONY
Filed May 22, 1968
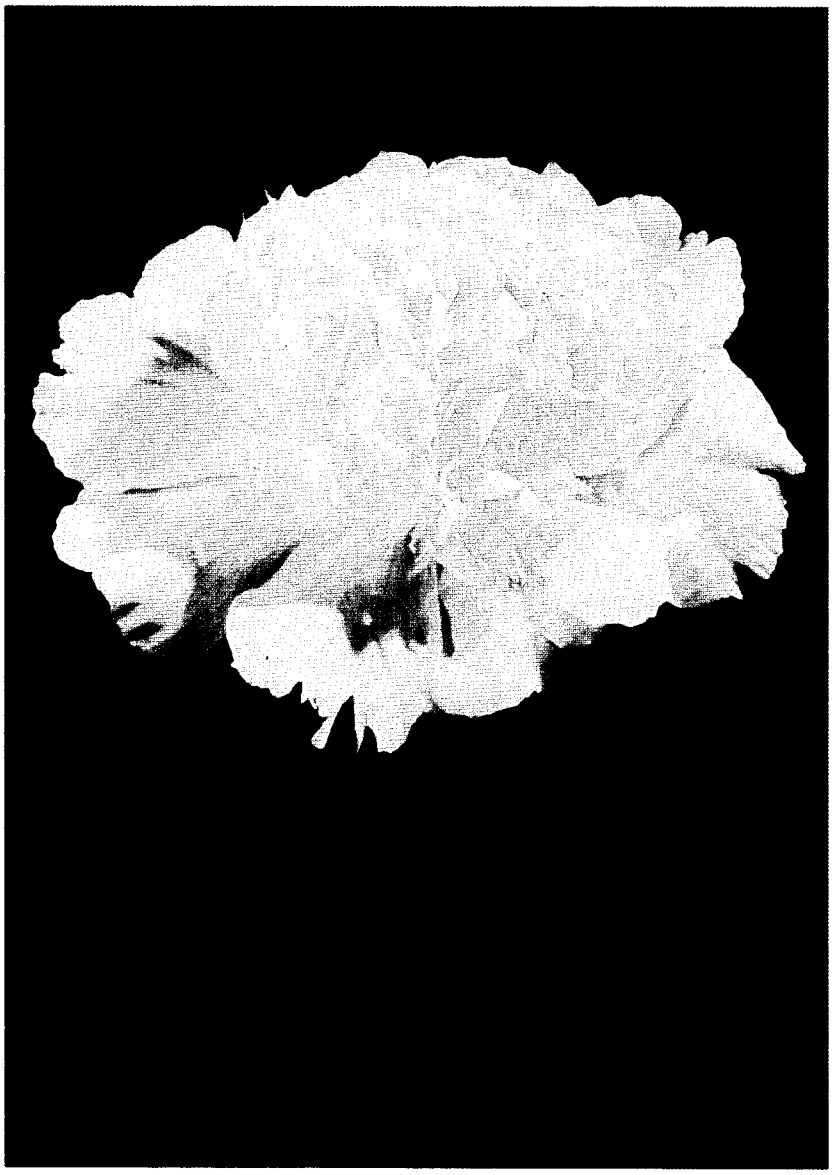
Inventor
Carl G. Klehm
By Hofgren, Wegner,
Allen, Stellman & McCord
Att'ys United States Patent Office Plant Pat. 2,955
Patented Dec. 16, 1969

2,955
PEONY PLANT

Carl G. Klehm, 3 E. Algonquin Road,
Arlington Heights, Ill. 60005

Filed May 22, 1968, Ser. No. 731,344
Int. Cl. A01h 5/02
U.S. Cl. Plt.—68 1 Claim The present invention relates to a new variety and strain of peony plant, especially characterized by the pleasing and unusual arrangement of the flower petals, the dainty appearance of the flower form, the unique yellow ribbing on white and soft pink petals, and the general health and vigor of the plant which makes it especially desirable for landscape use.

This peony variety was originated by me at my nursery in Arlington Heights, Ill. from a cross between Alice Harding (pollen parent—non-patented) and Mons. Jules Elie (seed parent—non-patented) by the process of hand pollination. This peony plant was asexually reproduced by me in Arlington Heights, Ill., by root division. Thousands of seedlings were developed as a result of this cross and from these thousands this particular peony plant was selected. It took seven years for the plant to produce its first bloom. The plant has been under constant observation and testing by me for fifteen (15) years.

This peony derives its unusual color combination from the gene pools of both parents. The seed parent, Mons. Jules Elie gave the variety its over-all health, its rich dark green foliage, color and the unique arrangement and shapes of the flower petals. The smooth bud and stiff stems so necessary for a good landscape selection can be attributed to Alice Harding (pollen parent).

The flower form itself is a dainty bomb-shape with an abnormally high crown. On the very top of this crown arise three to four crinkled petals. These petals protrude approximately ¾" over the general hemispherical shape of the crown. They are of the deepest pink to be found on the flower and have a yellow midrib extending from the base of the petal to about three-fourth of the way to the tip of the petals. The rest of the crown portion of the bomb has a basic white petal color with wider and more complete linear yellow midribs. The guard petals are a single overlapping row, the outer edges of which are crinkled and figured. They are of a pure white color with very faint pink speckles.

This peony variety is especially suitable for the home landscape and garden because of its enhancing dainty beauty, its ease of culture, its freedom from pests and diseases and its unfailing annual performance.

The accompanying drawing shows a typical specimen of an individual flower in color, as nearly true as reasonably possible in a color illustration of this character.

As a convenient summary, the following detailed description of this new peony variety is given with color terminology generally in accordance with Kornerup and Wanscher's 1961 edition of "Reinhold Color Atlas," except where general color terms are used.

Parentage:

*Seed parent.*—Mons. Jules Elie, from which this variety obtained its vigorous health, its outstanding rich dark green foliage, and the unique arrangement and shape of its flower petals.

*Pollen parent.*—Alice Harding, from which this variety obtains its smooth buds and stiff stems so necessary for good landscape plantings.

FLOWER

Blooming habit: Annually.

Bud:

*Size.*—Large 1½–1¾" on established plant.

*Form.*—Smooth even and round.

*Color.*—Soft pink 10A2.

*Sepals.*—Smooth green wrapped tightly around bud.

*Calyx.*—Polysepalous.

*Peduncle.*—None.

*Opening.*—Unfailing opening qualities—a yearly performer.

Bloom:

*Size.*—Medium large ⅞" when fully expanded.

*Borne.*—Singly on a terminal stem witth one to two usually small axillary buds.

*Forms.*—High crown bomb with one row of overlapping guard petals.

*Petalage.*—Crinkled and recurved—better than average fullness.

*Color.*—Guards 1A1 with slight 10A2 speckles; central tuft 9A2 soft pink; yelllow midribs 2A6–7; crown petals other than central tuft 10A1–2, darkening the more dorsal the petals are.

*Variegations and discolorations.*—None.

*Petals*:

*Texture.*—Thick, not affected by wet or hot weather.

*Appearance.*—Satiny inside and outside.

*Form.*—Recurved, crinkled and some patterned arrangement.

*Arrangement.*—Symmetrically-spaced around a central axis.

*Persistence.*—Long persistence but drop off cleanly.

*Fragrance.*—Mild, sweet peony scent.

*Lastingness.*—Depending on weather conditions from 1½ to 3 weeks.

Genital organs:

*Stamens—anthers.*—None.

*Stamens—filaments.*—None.

*Pollen.*—None.

*Styles.*—Rudimentary.

*Stigmas.*—Rudimentary.

*Ovaries.*—Rudimentary.

Fruit: None.

PLANT

Form: Herbaceous bush.

Growth: Vigorous strong (species *lactiflora*).

Foliage:

*Leaflets.*—Generally three.

*Size.*—10–12" long, 9–10" wide.

*Quantity.*—Average.

*Color.*—Rich green 29F8.

*Shape.*—Elliptically acute.

*Stem.*—Medium strong—generally 27–28" tall.

*Texture.*—Smooth dorsal pronounced central venation.

*Edge.*—Entire.

*Serration.*—None.

*Leaf stem.*—Petiolate attachment.

*Stipules.*—None.

*Disease resistance.*—Extremely resistant to leaf blotch and other bacterial diseases as observed during the fifteen (15) years of testing in Arlington Heights and surrounding areas.

I claim:

1. A new and distinct variety of peony plant characterized by its beautiful and dainty color combination; its unique petal shape and arrangement; and the health and hardiness of the variety as described herein.

No references cited.

ROBERT E. BAGWILL, Primary Examiner